United States Patent [19]

Kalt et al.

[11] Patent Number: 4,702,736
[45] Date of Patent: Oct. 27, 1987

[54] UNIVERSAL CLAMP

[75] Inventors: Glenda Kalt, 2640 Hollywood Blvd., Suite 200, Hollywood, Fla. 33020; Dale K. Straub, Los Angeles, Calif.; Peter Piwonka, Munich, Fed. Rep. of Germany

[73] Assignee: Glenda Kalt, Boca Raton, Fla.

[21] Appl. No.: 730,344

[22] Filed: May 3, 1985

[51] Int. Cl.⁴ ............................................. A61M 25/02
[52] U.S. Cl. .............................. 604/180; 128/DIG. 26
[58] Field of Search .................. 604/180, 179, 174; 188/DIG. 15, DIG. 26

[56] References Cited

U.S. PATENT DOCUMENTS

| | | |
|---|---|---|
| 2,707,953 | 5/1955 | Ryan . |
| 2,735,432 | 2/1956 | Hudson . |
| 3,161,199 | 12/1964 | Shaw . |
| 3,288,136 | 11/1966 | Lund . |
| 3,324,853 | 6/1967 | Czorny et al. . |
| 3,630,195 | 12/1971 | Santomieri . |
| 3,677,250 | 7/1972 | Thomas . |
| 3,696,920 | 10/1972 | Lahay . |
| 3,702,612 | 11/1972 | Schlesinger . |
| 3,826,254 | 7/1974 | Melbor . |
| 3,834,380 | 9/1974 | Boyd . |
| 3,918,446 | 4/1975 | Buttaravoli . |
| 3,972,321 | 8/1976 | Proctor . |
| 4,018,221 | 4/1977 | Rennie . |
| 4,088,136 | 5/1978 | Hasslinger et al. . |
| 4,122,857 | 10/1978 | Haerr . |
| 4,165,748 | 8/1979 | Johnson . |
| 4,329,984 | 5/1982 | Kervin . |
| 4,333,468 | 6/1982 | Geist . |
| 4,416,664 | 11/1983 | Womack . |
| 4,417,710 | 11/1983 | Adair . |
| 4,583,976 | 8/1986 | Ferguson . |
| 4,617,017 | 12/1986 | Hubbard et al. . |

Primary Examiner—Stephen C. Pellegrino
Attorney, Agent, or Firm—Dickstein, Shapiro & Morin

[57] ABSTRACT

A clamp for holding an article to an object including a base means for adhering the clamp to the object, a flap, securing means for securing the flap to the base means with the article positioned therebetween and resilient pad means having an adhesive surface for contacting the article. The securing means includes a first holding means for holding a first portion of the flap and a second holding means for holding a second portion of the flap. Both holding means may be releasable. The second holding means is spaced from the first holding means a sufficient distance along the flap for the article to lie between them. Resilient adhesive surfaces are provided on the flap and base means for contacting and adhering the article.

26 Claims, 15 Drawing Figures

UNIVERSAL CLAMP

BACKGROUND OF THE INVENTION

The present invention relates in general to a clamp for holding an article and more particularly to a medical clamp for holding a tube to a patient's body.

It is often necessary to clamp external and mesentery tubes to a medical patient's body, for example, feeding tubes, naso-gastric tubes, chest tubes, foley catheter as well as condom catheter tubes, dialysis tubes, angiocath and heparin lock set tubes, as well as other tubes used to introduce fluids into the body intravaneously or to introduce oxygen into the mouth or nose of a patient.

It is important that a tube clamp holds the tube firmly because movement of the tubes may cause discomfort to the patient. It is often necessary to remove the tube and replace it with another or to adjust the position of the tube. Therefore, it is desirable that the clamp be releasable so that the tube may be unclamped and reclamped without removing or replacing the entire clamp structure.

U.S. Pat. No. 3,826,254 discloses a clamp comprising an adhesive pad which folds back over itself to adhere a tube.

U.S. Pat. No. 4,165,748 discloses a tube clamp formed in one piece and adherable to a patient's body and having a center portion which folds around and clamps the tube by adhering to itself.

U.S. Pat. No. 4,333,468 discloses a clamp having a base having two raised portions to form between them a transverse groove. A tube is accepted to lie in the groove and a flap permanently affixed to the base at one end is extendable over the tube. Pressure sensitive adhesive covers the raised portions and the groove of the base as well as the flap underside. The flap is pressed onto the raised portions and the tube to adhere and clamp the tube in the groove.

Each of the foregoing clamps suffers the disadvantage that slight rotation or translation of the tube tends to break the adhesive bond. Thus secure holding of the tube is not effected.

U.S. Pat. No. 3,834,380 discloses a clamp including a slit tube which receives a rod-like article and is closed and kept closed by a flap attached to the tube at one end and secured at the other end. The tube is flexible and may be resilient. This device is unduly bulky and may cause discomfort to the patient and tends to lift the clamp tape off of the patient which causes further discomfort. Moreover, this device is insufficiently flexible for use in areas of the body where movement is likely and flexibility is desired. Such areas include the head and joint areas. This inflexibility may result in a tube being held in a wrong position. Moreover, this device depends on friction for holding a tube, and is therefore dependent upon the surface properties of the article or tube to be held to effect such a friction bond. If the surface of the article to be held is "slippery" relative to the material of the slit tube, the holding effect will be poor. A further disadvantage of this device is that only a small range of sizes of tubes may be held for a given slit tube size.

SUMMARY OF THE INVENTION

The present invention alleviates to a great extent the disadvantages of prior devices by providing a clamp for holding an article to an object including a base means for adhering the clamp to the object, a flap, securing means for securing the flap to the base means with the article positioned therebetween, and resilient pad means having an adhesive surface for contacting the article. In one aspect of the invention, the securing means includes a first holding means for holding a first portion of the flap and a second holding means for holding a second portion of the flap. The second holding means is spaced along the flap from the first holding means a sufficient distance for the article to lie between them. The resilient pad means is deformable such that slight rotational or translational movement will deform the pad rather than break the adhesive bond between the pad and the article.

It is an object of the present invention to provide a clamp for holding an article.

It is a further object of the present invention to provide a clamp having a resilient adhesive pad in contact with the held article to inhibit the braking of the adhesive bond as the result of rotational or translational movement of the article.

It is another object of the invention to provide a medical clamp to releasably hold a tube to allow removal of the tube and repositioning of the tube without removal of the clamp from the patient's body.

It is yet another object of the invention to provide a medical clamp yielding the foregoing advantages and that effectively holds a tube against transverse and rotational movement.

It is still another object of the present invention to provide a medical clamp yielding the foregoing advantages and that is simply and economically constructed.

It is a still further object of the present invention to provide a medical clamp yielding the foregoing advantages and that can clamp a variety of sizes of tubes.

DETAILED DESCRIPTION OF THE PREFERRED EMBODIMENTS

As referred to herein, the inner surfaces of various component parts of the preferred embodiments of the present invention are those surfaces oriented towards the object to which the clamp is adherred. Similarly, the outer surfaces of the various component parts of the preferred embodiment are those surfaces oriented away from such object. Such object may be any object but for medical clamps will most likely be the patient's skin, the patient's clothing, bandages, casts or the like.

Figure 1:
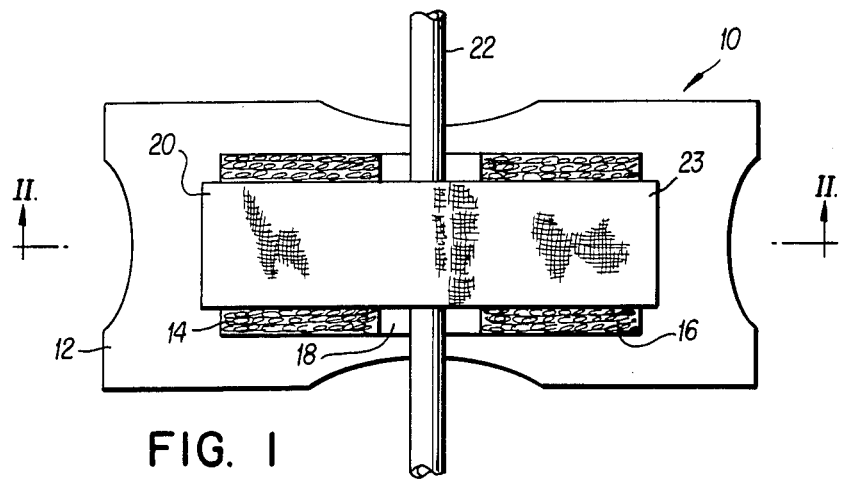
FIG. 1 is a plan view of a first embodiment of a medical clamp according to the present invention.
Figure 2:
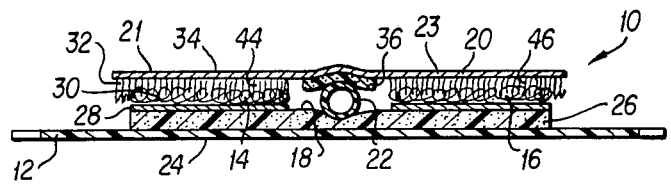
FIG. 2 is a view taken along section line II—II of FIG. 1.

Referring now to FIGS. 1 and 2 there is shown a medical clamp, generally designated by reference numeral 10, according to a first preferred embodiment of the present invention. In the first preferred embodiment, clamp 10 is particularly suitable for holding a tube 22 to the skin of a medical patient. The base means for adhering clamp 10 to the patient includes a base 12 that is preferably composed of medical grade tape such as 3M-1527L marketed by 3M Company under the registered trademark "Transtore". Base 12 is coated on its inner surface 24, with a medical grade adhesive, preferably a hypogenic synthetic acrylic pressure sensitive adhesive.

Flap 20 extends outside of tube 22 and is secured to base 12 by securing means to hold tube 22 therebetween. In the first preferred embodiment, securing means includes an adhesive pad 26 and hook and loop fastening material 32 and 30 as described in more detail below.

Flap 20 includes a hook base fabric 34 into which is woven hook fabric 32 of the securing means. In the preferred embodiment hook fabric 32 defines hook pads 44 and 46. Hook pad 44 is woven into a first portion 21 of flap 20 and hook pad 46 is woven into second portion 23 of flap 20. Hook fabric 32 is absent from region 38 of flap 20 between pads 44 and 46.

Adhesive pad 26 is positioned on the outer surface of base 12. Pad 26 is composed of a resilient material and is coated on both its outer and inner surfaces with a medical grade adhesive. Pad 26 is preferably a polyvinyl chloride foam such as 3M-1511 available from 3M Company. The thickness of pad 26 is preferably between five and two hundred mils and more preferably about thirty five mils.

First loop pad 14 and second loop pad 16 are composed of a loop material that includes loop fabric 30 and base fabric 28. Pads 14 and 16 are adherred at base fabric 28 by medical grade adhesive to the outer surface of pad 26. Loop pads 14 and 16 are adapted to mate with first hook pad 44 and second hook pad 46, respectively, which are woven to first portion 21 and second portion 23, respectively, of flap 20 to, with adhesive pad 26, secure flap 20 to base 12. The hook and loop materials are available from 3M Company under the registered trademark "Scotchmate".

In the first preferred embodiment, flap 20 may be constructed by removing hooks from stock hook material to form region 38. This may be accomplished by ultrasonic welding equipment and techniques. Alternatively, a separate flap material may be provided with individual hook pads, each including backing and hook fabric, adhered to the inner surface of such material in spaced relationship so as to form region 38.

In the first preferred embodiment the loop material has been provided to face outwards because loop material is typically softer than hook material and will not discomfort the patient if her skin should rub against it.

Tube 22 extends between pad 14 and pad 16 along the region 18 of pad 26. Hooks 32 are not present on flap 20 in region 38 in facing correspondence with region 18. Pad 36 which is similar in construction to resilient pad 26 and having adhesive inner and outer surfaces is adherred to the inner surface of flap 20 at region 38. Resilient pad 36 and region 18 of resilient pad 26 define the resilient pad means of the first preferred embodiment.

It has been found that the utilization of a resilient adhesive material such as 36 and 26 in contact with a tube provides a secure means for holding the tube against rotational or translational movement. This may be because in use the resilient material tends to deform and move with the tube when the tube is urged to rotate slightly or to translate slightly. Because the resilient material deforms, the bond of the adhesive with the tube is stressed to a lesser degree and is less likely to be broken. Significant deformation must occur before the resilient material will resist further deformation with such a force that the adhesive bond between the pad and the tube is broken. Accordingly, significant movement of the tube is possible prior to the breaking of the adhesive bond. Conversely, in prior clamps where no resilient adhesive pads are provided, any rotational or translational movement of the tube, with respect to the clamp adhesive surfaces, which movement may be caused by the bumping of the tube by the patient, may more likely result in the breaking of the adhesive bond holding the tube.

Figure 3:
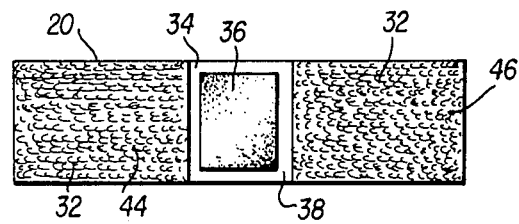
FIG. 3 is a view of the inner surface of flap 20 of FIG. 1.
Figure 4:
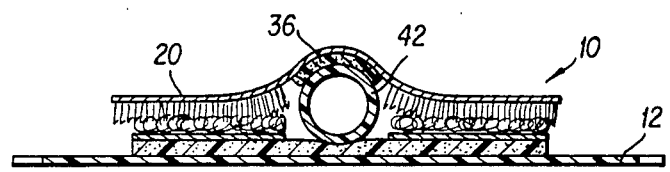
FIG. 4 is a view like FIG. 2 illustrating the clamping of a relatively larger tube.

FIG. 3 illustrates the inner surface of flap 20. FIG. 4 illustrates Clamp 10 holding tube 42 which is larger in diameter than tube 22 of FIG. 1.

Figure 5:
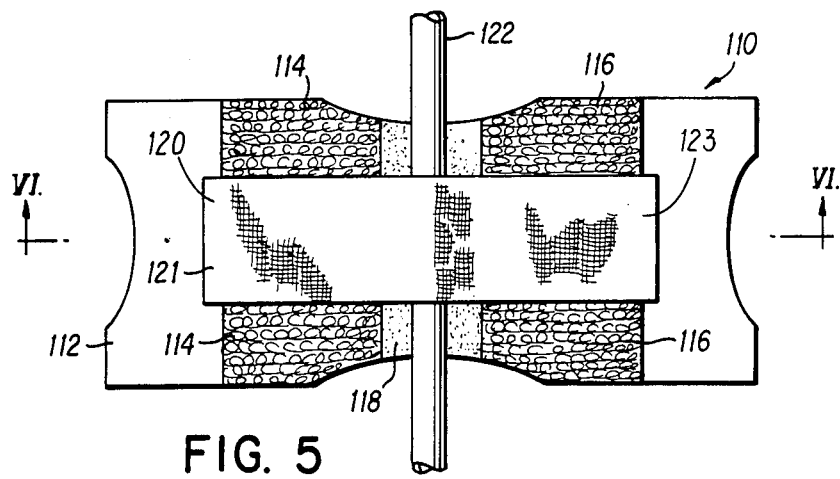
FIG. 5 is a plan view of a second embodiment of a medical clamp according to the present invention.
Figure 6:
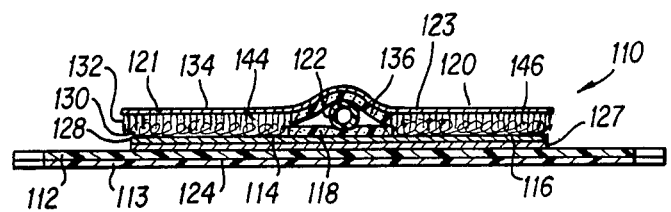
FIG. 6 is a view taken along section line VI—VI of FIG. 5.
Figure 7:
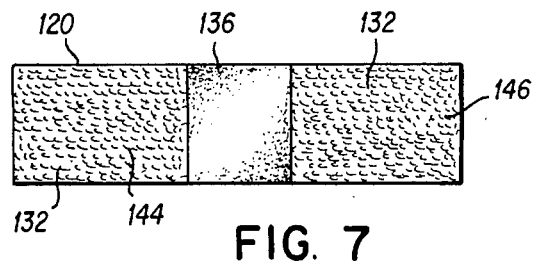
FIG. 7 is a view of the inner surface of flap 120 of FIG. 5.

Refer now to FIGS. 5 through 7 which illustrate a second preferred embodiment of the present invention. A clamp according to the second preferred embodiment of the invention, generally designated by reference numeral 110, is similar in construction to the first preferred embodiment described in conjunction with FIGS. 1 through 4, with the difference in the two embodiments residing primarily in the construction of the resilient pad means.

Clamp 110 includes base 112 that is preferably composed of medical grade tape similar to that described for the first preferred embodiment. Base 112 is coated on its inner surface 124 with a medical grade adhesive. Flap 120 extends outside of tube 122, the article to be held, and is secured to base 112 by securing means to hold tube 122 therebetween.

In the second preferred embodiment, the securing means includes a transfer tape 127 which has adhesive applied to both sides, the outer and inner sides, to function to hold loop fabric backing 128 to base 112. With reference to FIGS. 5 and 6, preferably transfer tape 127 underlies the whole area of loop fabric backing 128 to securely hold the loop backing fabric to base 112. Loop fabric backing 128 and loop fabric 130 woven thereto, extends through loop pad 114, resilient pad 118, and loop pad 116.

Resilient pad 118 is formed by applying a hot melt adhesive to the loop fabric 130 such that the applied adhesive extends up slightly above the top of the loops. When the hot melt adhesive cools and cures, it forms a resilient pad with an adhering outer surface. Medical grade hot melt adhesives suitable for this purpose include numbers DD5800, DD5900 and DD5914 available from H. Fuller Adhesive Company. Preferably, the applied hot melt adhesive, when set up, or cured, will extend about one sixteenth of an inch above the loop material surface.

Flap 120 of the second preferred embodiment clamp 110, is made of hook fabric 132 woven into hook backing material 134. Similar to the loop material of the second preferred embodiment the hook material extends over the whole inside surface of flap 120 and the resilient pad 136 is formed by applying hot melt adhesive in the above-described fashion. Hook pad 144 to one side of hot melt adhesive resilient pad 136 is woven to a first portion of flap 120 and hook pad 146 to the other side of hot melt adhesive resilient pad 136 is woven to a second portion of flap 120. The first holding means for holding a first portion of flap 120 includes hook pad 144, loop pad 114, loop fabric backing 128, and transfer tape 127. The second holding means for holding a second portion of flap 120 includes hook pad 116, loop pad 146, loop fabric backing 128 and transfer tape 127. The first and second holding means function to releasably secure flap 120 to base 112.

Also illustrated in FIG. 6 is liner 113 which extends on the inner portion of base 112 to protect the adhesive surface thereof. When the clamp is to be used and to be adherred to an object such as the patient or piece of equipment or whatever, liner 113 is removed and fresh adhesive on surface 124 of base 112 is exposed.

Similarly, liners may be provided for covering the resilient adhesive pads 136 and 118 until those adhesive surfaces are to be utilized. This holds true for any of the embodiments herein, such liners may be provided where appropriate.

Figure 8:
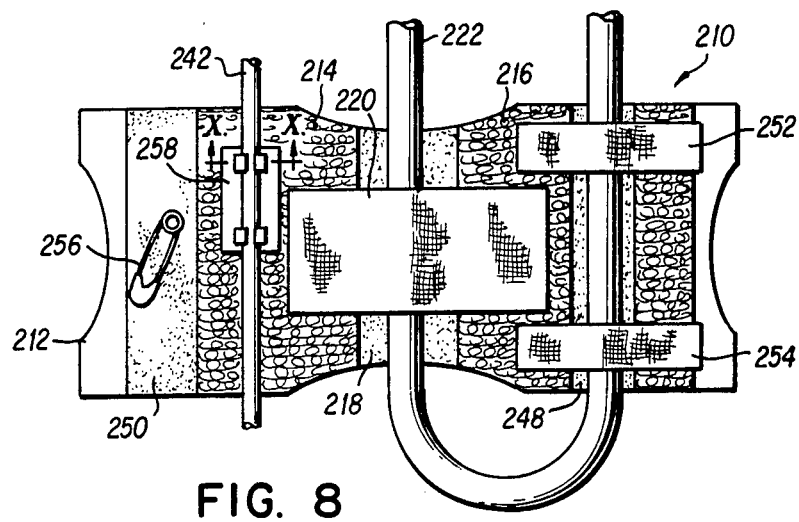
FIG. 8 is a plan view of a third embodiment of a medical clamp according to the present invention.
Figure 9:
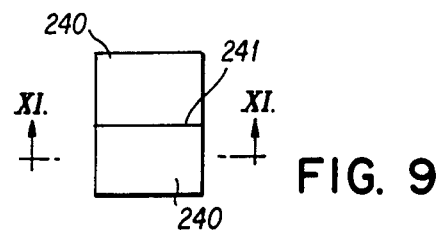
FIG. 9 is a plan view of a remote fastener used with the preferred embodiment of the present invention.
Figure 10:
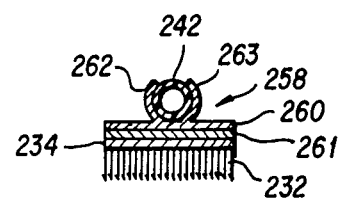
FIG. 10 is a view taken along section line X—X of FIG. 8.

Refering now to FIGS. 8 through 10, therein is illustrated a third preferred embodiment of the present invention. Clamp 210 illustrated therein, is similar in construction to either the first preferred embodiment or the second preferred embodiment, or a combination thereof, except that a plurality of adhesive pads are provided in parallel transverse arrangement.

Adhesive pad 250, adhesive pad 218 and adhesive pad 248 are provided as shown. Adhesive pads 218 and 248 each have loop material on either side. Loop pad 214 and loop pad 216 lie on either side of adhesive pad 218. Flap 220 extends across adhesive pad 218 and is secured to base 212 at both ends. Loop pad 216 and loop pad 211 are positioned on either side of adhesive pad 248. Note in this particular embodiment that tube 222 is clamped by flap 220 and turns and extends back again and is held to pad 248 by flaps 252 and 254.

Adhesive pad 250 does not have a loop pad on both sides. Pad 250 is useful for adhering objects to base 212 where a flap is not required. As shown, safety pin 256 is so adherred.

Another aspect of the present invention is illustrated by remote fastener 258 which is holding tube 242. Fastener 258 or others like it may be utilized to fasten instruments, thermometers, tubes, needles, wires, or whatever else may be required to be held out of the way in a hospital setting or other setting.

Referring to FIG. 10, there is shown a cross section of fastener 258. Fastener 258 includes base 260 having fingers 262 and 263 which extend and are angled towards one another to hold tube 242 there between. Base 260 is held to hook fabric backing 234 by transfer tape 261. Hook fabric 232 is woven into hook fabric backing 234.

Figure 11:
FIG. 11 is a view taken along section line XI—XI of FIG. 9.

A remote fastener 258 may come assembled as illustrated in FIG. 10, or alternatively may come as illustrated in FIGS. 11 and 9, with transfer tape 261 protected by liner 240. A slit 241 is provided in liner 240, and when the remote fastener is to be used, the liner 240 is removed and a base similar in construction to 260, or of some alternate construction adapted for a particular holding need, is attached to transfer tape 261 and thereby adherred to hook fabric and backing 232, 234. The remote fastener may now be attached to any available loop material to clamp the held article such as tube 242 an object.

Yet another and fourth embodiment of the present invention is illustrated by FIGS. 12 through 15. The fourth preferred embodiment of a medical clamp, general designated by reference numeral 310, is similar in construction to the embodiment of FIG. 1 except that flap 320 is held at its first portion 321 in a non-releasable manner.

Figure 12:
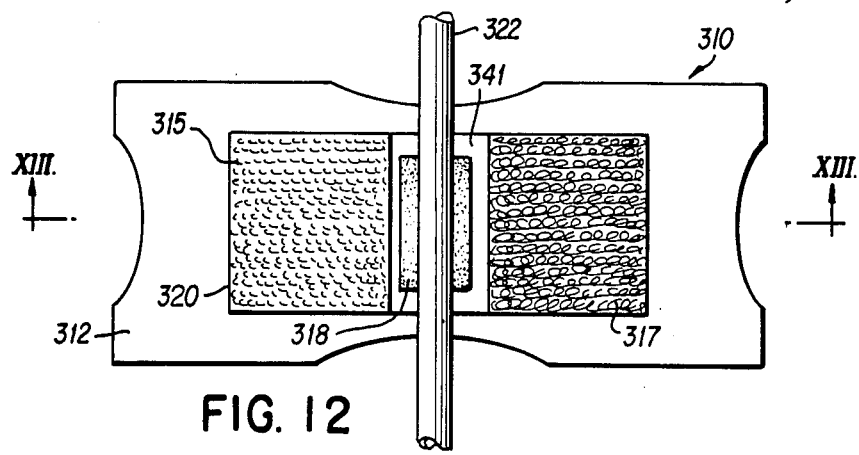
FIG. 12 is a plan view of a fourth preferred embodiment of the present invention showing the clamp open.
Figure 13:
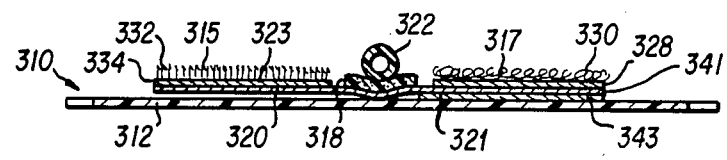
FIG. 13 is a view taken along section line XIII—XIII of FIG. 12.

Referring particularly to FIGS. 12 and 13, therein is shown a medical clamp according to the fourth preferred embodiment in its opened position. Flap 320 is composed of a substrate, preferably nylon, having on a second portion hook fabric 332 woven to hook fabric backing 334 to form hook pad 315. Hook pad 315 is adherred to second portion 323 of flap 320. The nylon substrate that forms flap 320 extends past the first portion 321 of flap 320 and is adherred at the fixed portion 341 of the substrate to base 312 by transfer tape 343. Loop fabric 330 woven to loop fabric backing 328 is adherred to a fixed portion 341 of the substrate and forms loop pad 317. The area of substrate 341 which lies between hook pad 315 and loop pad 317 is provided with resilient pad 318. Tube 322 lies on resilient adhesive pad 318 in the open position of the fourth preferred embodiment as illustrated in FIGS. 12 and 13.

Figure 14:
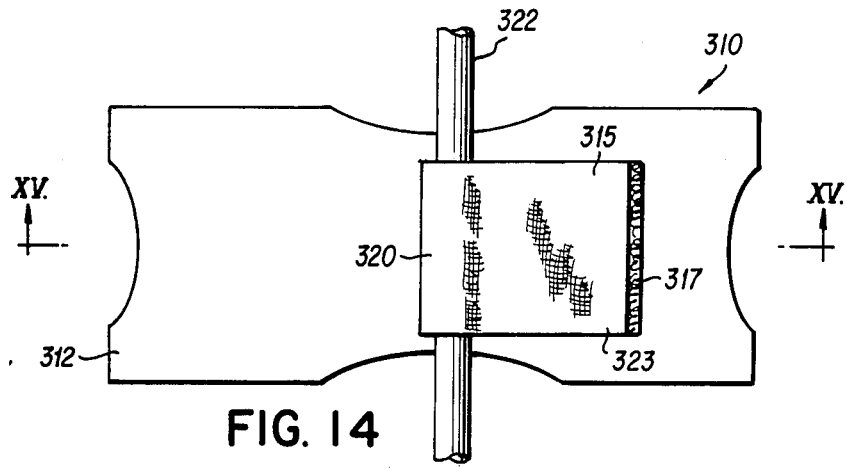
FIG. 14 is a view like FIG. 12 showing the clamp closed.
Figure 15:
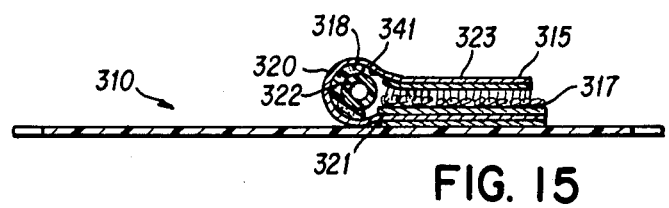
FIG. 15 is a view taken along section line XV—XV of FIG. 14.

Referring now to FIGS. 14 and 15, clamp 310 is shown in its closed position with flap 320 wrapped over tube 322 such that hook pad 315 mates with loop pad 317 to thereby hold the second portion 323 of flap 320 with transfer tape 321 and the affixed portion of substrate 341 to base 312. In the closed position resilient pad means, resilient pad 318 having an adhesive surface which contacts tube 322 functions to clamp tube 322 against rotation and translation.

In the preferred embodiments of the invention medical grade adhesive and a hook and loop material is provided to secure flap 20 to base 12, however the present invention is not limited thereto, and other securing means may be used.

What is claimed and desired to be protected by Letters Patent of the United States is:

1. A clamp for holding an article to an object comprising:
   (a) base means for adhering the clamp to the object;
   (b) flap means formed separately from said base means;
   (c) securing means for securing each end of said flap mens to said base means and including a first holding means for holding a first end of said flap means to said base means and a second holding means for holding a second end of said flap means to said base means, said second holding means being spaced from said first holding means a sufficient distance for the article to extend therebetween, said first and second holding means being completely releasable and reattachable to said base means such that said flap can be completely separated from said base means; and (d) a resilient pad means having an adhesive surface located between said first and said second holding means for contacting said article whereby said adhesive surface is movable with the article with respect to said flap means to some extent due to the deformation of said flap means without breaking the contact.

2. A clamp as in claim 1 further comprising an outer resilient pad adherred to said flap between said first and second portions, said outer resilient pad having an adhesive surface for contacting the positioned article positioned between the flap and the base means.

3. A clamp as in claim 1 wherein at least one of said first and second releasable holding means includes a hook material and a loop material.

4. A clamp as in claim 3 wherein said securing means further includes a resilient inner pad positioned between the outer surface of said base and the inner surface of either said hook material or said loop material.

5. A clamp as in claim 4 wherein said inner pad extends over said base means between said first and second releasable holding means, said inner pad having an adhesive surface for contacting said positioned article.

6. A clamp as in claim 5 further comprsing an outer resilient pad adherred to said flap between said first and second portion and having an adhesive surface for contacting said positioned article.

7. A clamp for holding a rod-like article to an object comprising:
 (a) base means for adhering the clamp to the object;
 (b) flap means formed separately from said base means having an article contact surface and an outer protective surface;
 (c) securing means for securing said flap to said base means with a rod-like article positioned therebetween, and including a first holding means for holding a first end of said flap and a second holding means for holding a second end of said flap, said second holding means being spaced from said first holding means a sufficient distance for the rod-like article to extend therebetween; said first and second holding means being completely releasable and reattachable to said base means such that said first and second holding means can be completely separated from said base means;
 (d) an outer resilient pad affixed to said article contact surface of said flap means between said first and second portions and having an adhesive surface for contacting said positioned rod-like article to form an adhesive bond therewith, said adhesive surface movable with the article with respect to said flap to some extend due to the deformation of said resilient pad without breaking the adhesive bond.

8. A clamp for holding an article to an object comprising:
 (a) base means for holding the clamp to the object;
 (b) flap means formed separately from said base means having an article contact surface and an outer protective surface;
 (c) securing means for securing said flap to said base means with the article positioned to be held by said flap means to said base means;
 (d) resilent pad means for contacting and securely holding the positioned article and allowing some movement thereof relative to said flap means and including a resilient material affixed to a surface fo said flap means and positioned between said flap means and the article, and said resilient material having an adhesive surface located between said securing means for contacting the positioned article to form an adhesive bond therewith, said adhesive surface movable with the article with respect to said surface of said flap means to some extent due to the deformation of said resilient material without breaking the adhesive bond.

9. A clamp as in claim 8 wherein said securing means includes a first holding means for holding a first portion of said flap and a second holding means for holding a second portion of said flap.

10. A claim as in claim 9 wherein said resilient pad means comprises an outer resilient pad adherred only to an area of said flap between said first and second portions, said outer resilient pad having an adhesive surface for contacting said positioned article.

11. A clamp as in claim 10, wherein said area of said flap is larger than said outer resilient pad.

12. A clamp as in claim 9 wherein at least one of said first and second holding means includes a hook material and a loop material.

13. A clamp as in claim 12 wherein said securing means further includes a resilient inner pad positioned between the outer surface of said base and the inner surface of either said hook material or said loop material.

14. A clamp as in claim 13 wherein said resilient pad means includes an inner resilient pad extending over said base means between said first and second releasable holding means, said inner pad having an adhesive surface for contacting said positioned rod-like article.

15. A clamp as in claim 14 wherein said resilient pad means includes an outer resilient pad adhered to said flap between said first and second portion and having an adhesive surface for contacting said positioned rod-like article.

16. A clamp as in claim 12 further comprising remote fastening means for fastening at least one additional article to said clamp, and including a hook material or aloop material to mate with an outer surface of one of said first and second holding means.

17. A clamp as in claim 9 wherein said first holding means is releasable and said second holding means is non-releasable.

18. A clamp as in claim 17 wherein said second holding means includes a first substrate and said flap includes a second substrate attached to said first substrate by said first holding means.

19. A clamp as in claim 18 wherein said first substrate is integral with said second substrate.

20. A clamp as in claim 18, wherein said first holding means includes a hook material adherred to said second substrate and a loop material adherred to said first substrate.

21. A clamp as in claim 20, wherein said first substrate includes an area between said hook pad and said second substrate and said resilient pad means is adherred to said area.

22. A clamp as in claim 21, wherein the area of said first substrate and said second substrate taken together is smaller than the area of said base and wherein said second subsstrate is adherred to said base in a position such that said flap does not extend significantly beyond the edges of said base when extended in the open position.

23. A clamp as in claim 8 wherein said resilient material includes a foam material.

24. A clamp as in claim 8 wherein said resilient material includes a hot melt adhesive material.

25. A clamp as in claim 24, wherein said hot melt adhesive forms said adhesive surface.

26. A clamp as in claim 8, wherein said resilient material has a flap surface being generally parallel with said adhesive surface and defining a resilient material thickness therebetween, said resilient material being affixed at said flap surface to said flap, said resilient material being deformed through its thickness upon movement of the article adhesively bonded thereto relative to said flap such that said adhesive surface moves to a greater extent than said flap surface.

* * * * *

UNITED STATES PATENT AND TRADEMARK OFFICE
CERTIFICATE OF CORRECTION

PATENT NO. : 4,702,736

DATED : Oct. 27, 1987

INVENTOR(S) : Glenda Kalt, Dale K. Straub, Peter Piwonka

It is certified that error appears in the above-identified patent and that said Letters Patent is hereby corrected as shown below:

Column 6, line 58, change "mens" to --means--.

Column 7, line 24, change "comprsing" to --comprising--;

line 52, change "extend" to --extent--;

line 63, change "resilent" to --resilient--;

line 66, change "fo" to --of--.

Column 8, line 12, change "claim" (first instance) to --clamp--;

line 41, change "aloop" to --a loop--;

line 63, change "subsstrate" to --substrate--.

Signed and Sealed this

Thirtieth Day of August, 1988

*Attest:*

DONALD J. QUIGG

*Attesting Officer*     *Commissioner of Patents and Trademarks*